(12) United States Patent
Richards et al.

(10) Patent No.: US 9,474,768 B1
(45) Date of Patent: Oct. 25, 2016

(54) LUBRICANT FORMULATIONS

(71) Applicant: Reoxcyn Discoveries Group, Inc., Salt Lake City, UT (US)

(72) Inventors: Kurt Richards, Herriman, UT (US); Andrew Hoover, Pleasant Grove, UT (US)

(73) Assignee: Reoxcyn Discoveries Group, Inc., Salt Lake City, UT (US)

( * ) Notice: Subject to any disclaimer, the term of this patent is extended or adjusted under 35 U.S.C. 154(b) by 0 days.

(21) Appl. No.: 15/158,442

(22) Filed: May 18, 2016

(51) Int. Cl.
*A61K 33/20* (2006.01)
*A61K 47/48* (2006.01)
*A61K 47/02* (2006.01)
*A61K 9/00* (2006.01)

(52) U.S. Cl.
CPC ............ *A61K 33/20* (2013.01); *A61K 9/0034* (2013.01); *A61K 47/02* (2013.01); *A61K 47/48192* (2013.01)

(58) Field of Classification Search
None
See application file for complete search history.

(56) References Cited

U.S. PATENT DOCUMENTS

| | | | |
|---|---|---|---|
| 4,671,955 A * | 6/1987 | Palinczar | A61K 8/731 424/47 |
| 4,956,184 A | 9/1990 | Kross | |
| 6,114,398 A | 9/2000 | Ratcliff | |
| 9,175,141 B2 | 11/2015 | Wray et al. | |
| 2005/0089537 A1 | 4/2005 | Birnholz | |
| 2007/0020213 A1* | 1/2007 | Tamarkin | A61K 8/046 424/70.1 |
| 2007/0172412 A1 | 7/2007 | Hratko et al. | |
| 2007/0281008 A1 | 12/2007 | Lin et al. | |
| 2009/0028811 A1 | 1/2009 | Potter | |
| 2010/0012132 A1 | 1/2010 | Harrison et al. | |
| 2015/0246131 A1 | 9/2015 | Romanoschi et al. | |
| 2015/0250704 A1 | 9/2015 | Romanoschi et al. | |

* cited by examiner

*Primary Examiner* — Brian Gulledge
(74) *Attorney, Agent, or Firm* — Knobbe Martens Olson & Bear LLP

(57) ABSTRACT

A composition for lubricant formulations is disclosed. The composition may include hypochlorite, dimethicone, and an emulsifier for improvement of lubricity. Methods of making and using the lubricant formulations are also disclosed.

19 Claims, No Drawings

LUBRICANT FORMULATIONS

FIELD OF THE DISCLOSURE

The present disclosure relates generally to lubricant compositions including antimicrobial agents. More specifically, the present disclosure is related to personal lubricants having hypochlorite, or acids or salts thereof, a silicone polymer, and one or more emulsifiers. The disclosure also relates to methods of making and using the lubricant.

BACKGROUND

Lubricants are useful generally for providing lubricity to various instruments and/or parts of the body, thereby reducing friction. For example, medical or surgical lubricants are useful for providing lubrication for decreasing the discomfort to a patient during certain medical and surgical procedures, including, for example, rectal or vaginal examinations. Personal lubricants function similarly, and can be used, for example, for intimate contact, by increasing lubricity and comfort during sexual intimacy.

Personal lubricants are of various types, with each type having different advantages. Water-based lubricants are water-soluble, and generally include water and a cellulose or glycerin solution. Oil-based lubricants are derived from either synthetic or natural oils, and can include, for example, a petroleum ingredient, such as petroleum jelly. Silicone-based lubricants are manufactured from synthetic chemical compounds, and do not contain water. Silicone-based lubricants are commonly formulated with a silicone ingredient, such as dimethicone or other polymeric organosilicon compound. Additional lubricants include hybrid lubricants, which may be formulated with water and silicone. Certain lubricants also further include sensory enhancing agents, that provide, for example, a warming or cooling sensation, or that provide a variety of odors or flavors.

Lubricants can be used as a stand-alone product for use during sexual intimacy, or have been used in combination with other products, such as with medical devices or with condoms, which facilitates penetration or insertion of the product. For example, personal lubricants may be used alone or in combination with condoms or other devices to improve lubrication and comfort during sexual intimacy. Surgical or medical lubricants or gels may be used for medical purposes such as speculum insertion or introduction of a catheter, ultra sounds, or other medical devices.

Personal lubricants have been developed that prevent or stop the development of itching from the vagina or other body parts. For example, U.S. Pat. No. 6,114,398 describes a personal lubricant having $ClO_2$, which is effective for the prevention of itching by eliminating *Candida* species.

Vaginal itching is a common complaint among women. Vaginal itching primarily originates from *Candida albicans*, a diploid fungus that grows as both a yeast and as a filamentous cell. *C. albicans* is the most common and possibly the most important causative agent of human fungal infections (Edmond, M. B., et al. 1999, Clin. Infect. Dis. 29:239-244). *C. albicans* is a major opportunistic pathogen of immunocompromised hosts, including AIDS patients and patients undergoing chemotherapy, patients who have had tissue transplants, and patients with central venous catheters. Studies indicate that up to ninety percent of AIDS patients suffer from oropharyngeal and esophageal candidiasis, in which *C. albicans* is the major causative agent (Schmidt-Westhausen, A., et al., 1991, J. Oral Pathol. Med. 20:467-472). *C. albicans* is a commensal of human mucosal surfaces. *C. albicans* causes a wide variety of diseases including oral thrush and disseminated candidiasis. Systemic fungal infections have emerged as important causes of morbidity and mortality in immunocompromised patients (e.g., as a result of AIDS, cancer chemotherapy, organ or bone marrow transplantation). In addition, hospital-related infections in patients not previously considered at risk (e.g., patients in an intensive care unit) have become a cause of major health concern. *C. albicans* is also the major fungus that colonizes medical implants, causing device-associated infections with high mortality. (Kojic E. M., Darouiche R. O.: *Candida* Infections of Medical Devices. Clin Microbiol Rev 2004, 17:255-267; Nobile et al., Critical Role of Bcr1-dependent Adhesins in *C. albicans* Biofilm Formation In Vitro and In Vivo. PLoS Pathog. 2006, 2: e63). Infections involving medical devices are notoriously difficult to eliminate and generally necessitate removal of the device. *C. albicans* colonizes the surfaces of catheters, prostheses, and epithelia, forming biofilms that are extremely resistant to antifungal drugs. Mature *C. albicans* biofilms show a complex three-dimensional architecture with extensive spatial heterogeneity, and consist of a dense network of yeast, hyphae and pseudo hyphae encased within a matrix of exopolymeric material.

SUMMARY

The present disclosure describes lubricant formulations and compositions having hypochlorite, or acids and salts thereof, a silicone polymer, and an emulsifier. Also described are methods of making and using the lubricant formulations.

In some embodiments is provided a lubricant having hypochlorite, an emulsifier, and a silicone polymer. In some embodiments, the silicone polymer is dimethicone.

In some embodiments is provided a personal lubricant including hypochlorite or acids or salts thereof, and a silicone polymer. In some embodiments, the hypochlorite is hypochlorous acid (HClO). In some embodiments, the hypochlorite is a hypochlorite salt, such as NaClO, KClO, or $Ca(ClO)_2$. In some embodiments, the silicone polymer is a polymeric organosilicon compound. In some embodiments, as the polymeric organosilicon compound is dimethicone.

In some embodiments, the lubricant composition further includes, for example, sodium magnesium silicate, sodium phosphate monobasic, water, buffer, sodium chloride, or combinations thereof.

In some embodiments, the lubricant includes hypochlorite. In some embodiments, the hypochlorite is a salt or acid of hypochlorite, or a hypochlorite solution. In some embodiments, a final concentration of hypochlorite in the lubricant is about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, the final concentration of hypochlorite in the lubricant is about 50 to 100 ppm. In some embodiments, the final concentration of hypochlorite in the lubricant is about 75 ppm.

In some embodiments, the emulsifier is sodium phosphate. In some embodiments, the emulsifier is present in the lubricant in an amount of about 0.05%, 0.1%, 0.2%, 0.3%, 0.4%, 0.5%, 1%, 1.5%, 2%, or 2.5% w/v or within a range defined by any two of the aforementioned amounts. In some embodiments, the emulsifier is present in the lubricant in an amount of about 0.2% w/v.

In some embodiments, the silicone polymer is dimethicone. In some embodiments, the silicone polymer is present in the lubricant in an amount of about 0.5%, 1%, 5%, 10%, 15%, 20%, 30%, 40%, or 50% w/v or within a range defined by any two of the aforementioned amounts. In some embodiments, the silicone polymer is present in the lubricant in an amount of about 10% w/v.

In some embodiments, the lubricant further includes sodium magnesium silicate, water, or buffer or combinations thereof. In some embodiments, the sodium magnesium silicate is present in the lubricant in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v or within a range defined by any two of the aforementioned amounts. In some embodiments, the sodium magnesium silicate is present in the lubricant in an amount of about 3.25% w/v. In some embodiments, the water and/or buffer makes up the balance of the lubricant, and includes about 20%, 30%, 40%, 45%, 50%, 55%, 56%, 57%, 58%, 59%, 60%, 61%, 61.55%, 62%, 62.5%, 63%, 65%, 70%, 75%, 80%, or 90% w/v or within a range defined by any two of the aforementioned amounts.

In some embodiments is provided a lubricant, wherein the lubricant includes a hypochlorite solution in an amount of about 25% w/v. In some embodiments, the hypochlorite solution includes about 300 ppm hypochlorite, dimethicone in an amount of about 10% w/v, sodium phosphate in an amount of about 0.2% w/v. In some embodiments, the lubricant further includes sodium magnesium silicate in an amount of about 3.25% w/v and water and/or buffer in an amount of about 61.55% w/v. In some embodiments, the water and/or buffer makes up all or substantially all of the balance of the lubricant.

In some embodiments is provided a lubricant including about 75 ppm hypochlorite, about 10% w/v dimethicone, and optionally 0.2% w/v sodium phosphate. In some embodiments, the lubricant further includes sodium magnesium silicate and water. In some embodiments, the personal lubricant may further include a buffer.

In some embodiments, the lubricant as disclosed herein is characterized in having an osmolality by vapor pressure of about 10, 20, 30, 35, 36, 37, 38, 39, 40, 41, 42, 43, 44, 45, 46, 47, 48, 49, 50, 55, 60, 70, 80, 90, or 100 mmol/kg, or within a range defined by any two of the aforementioned amounts. In some embodiments, the osmolality by vapor pressure is about 38 mmol/kg. In some embodiments, the osmolality by vapor pressure is about 49 mmol/kg. In some embodiments, the lubricant is characterized in having an osmolality by freezing point depression of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, or within a range defined by any two of the aforementioned amounts. In some embodiments, the osmolality by freezing point depression is about 22 mOsm/kg. In some embodiments, the osmolality by freezing point depression is about 54 mOsm/kg.

In some embodiments is provided a method of making the lubricant formulation. In some embodiments, the method includes providing hypochlorite. In some embodiments, the hypochlorite is provided as a hypochlorite acid or salt. In some embodiments, the hypochlorite is provided as a hypochlorite solution. In some embodiments, the method of making the lubricant includes providing hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is provided in an amount of about 50 to 100 ppm. In some embodiments, the hypochlorite is provided in an amount of about 75 ppm.

In some embodiments, the method of making the lubricant includes providing a hypochlorite solution. In some embodiments, the hypochlorite solution is prepared from hypochlorite acids or salts. In some embodiments, the hypochlorite salt is sodium hypochlorite. In some embodiments, the hypochlorite solution is prepared from sodium chloride. In some embodiments, the method includes running sodium chloride solution through electrolysis. In some embodiments, the sodium chloride solution is provided in an amount of about 0.1%, 0.15%, 0.2%, 0.25%, 0.3%, 0.35%, or 0.4% w/v. In some embodiments, the sodium chloride is 0.28%, and the resulting hypochlorite solution is about 300 ppm. In some embodiments, the method of making the lubricant includes diluting the hypochlorite solution to provide hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is diluted to an amount of about 50 to 100 ppm. In some embodiments, the hypochlorite is diluted to an amount of about 75 ppm.

In some embodiments, the method of making the lubricant further includes providing a silicone polymer. In some embodiments, the silicone polymer is dimethicone. In some embodiments, the silicone polymer is provided in an amount of about 0.5%, 1%, 5%, 10%, 15%, 20%, 30%, 40%, or 50% w/v, or within a range defined by any two of the aforementioned amounts. In some embodiments, the silicone polymer is provided in an amount of about 10% w/v.

In some embodiments, the method further includes providing an emulsifier. In some embodiments, the emulsifier is sodium phosphate. In some embodiments, the emulsifier is provided in an amount of about 0.05%, 0.1%, 0.2%, 0.3%, 0.4%, 0.5%, 1%, 1.5%, 2%, or 2.5% w/v or within a range defined by any two of the aforementioned amounts. In some embodiments, the emulsifier is provided in an amount of about 0.2% w/v.

In some embodiments, the method of making the lubricant further includes providing sodium magnesium silicate, water, or buffer or combinations thereof. In some embodiments, the sodium magnesium silicate is provided in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v or within a range defined by any two of the aforementioned amounts. In some embodiments, the sodium magnesium silicate is provided in an amount of about 3.25% w/v. In some embodiments, the water and/or buffer is provided in an amount to make up all or substantially all of the balance of the lubricant, and is provided in an amount of about 20%, 30%, 40%, 45%, 50%, 55%, 56%, 57%, 58%, 59%, 60%, 61%, 61.55%, 62%, 62.5%, 63%, 65%, 70%, 75%, 80%, 90% or 95% w/v or within a range defined by any two of the aforementioned amounts.

In some embodiments is provided a method of using a lubricant. In some embodiments, the method includes providing the lubricant and applying the lubricant. In some embodiments, the lubricant is provided as a ready-to-use formulation that includes hypochlorite or acids or salts thereof, silicone polymer, and an emulsifier, and further may include sodium magnesium silicate, water, or buffer. In some embodiments, the lubricant is provided in portions, and further additions and/or mixing is required prior to use. In some embodiments, the lubricant is applied in the penile or vaginal regions. In some embodiments, the lubricant is applied on a condom or other device. In some embodiments, the lubricant is applied multiple times daily, once daily, multiple times weekly, once weekly, multiple times monthly, or once monthly, or within a time frame defined by any two of the aforementioned time frames. In some embodiments, the lubricant is applied liberally. In some embodiments, the lubricant is applied meagerly.

In some embodiments is provided a method of using a lubricant for increasing comfort and lubricity. In some embodiments, the increase in comfort and lubricity is experienced during sexual intimacy. In some embodiments, the lubricant is used alone or in combination with condoms or other devices.

In some embodiments is provided a method of using a lubricant for the cessation, amelioration, prevention, or inhibition of the development of itching from the vagina or other body parts by eliminating microbial causing infections.

In some embodiments is provided a method of using the lubricant composition to stop a fungal infection. In some embodiments, the fungal infection is caused by a yeast of the *Candida* genus. In one embodiment, the yeast is of the *Candida albicans* species. In other embodiments, the *Candida* yeast may be of the *Candida dubliniensis, Candida parapsilosis, Candida tropicalis, Candida kerfyr, Candida guilliermondii, Candida inconspicua, Candida famata, Candida glabrata, Candida krusei, Candida lusitaniae*, or other *Candida* species, or combinations thereof. In some embodiments, the lubricant composition is used to stop a viral infection.

DETAILED DESCRIPTION OF CERTAIN INVENTIVE EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Lubricants, including personal lubricants are described herein that are useful for increasing lubricity. In some embodiments, the personal lubricant is useful for penile and/or vaginal application for increasing lubricity and for enhancing the ease and comfort of sexual intimacy, and for supplementing the body's natural lubrication. In some embodiment, the personal lubricant may be used alone or in combination with condoms or other devices to improve lubrication and comfort during sexual intimacy. In some embodiments, lubricants may be useful for treating, ameliorating, or reducing the itchiness associated with fungal, viral, or other skin conditions. In some embodiments, the personal lubricant is a hybrid-based lubricant that includes water and silicone. In some embodiments described herein are methods of making and using the lubricant formulations.

DEFINITIONS

Unless defined otherwise, technical and scientific terms used herein have the same meaning as commonly understood by one of ordinary skill in the art to which the present disclosure belongs. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In some embodiments, the "purity" of any given agent (for example, dimethicone or hypochlorous acid) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by analytical chemistry techniques.

As used herein, the terms "function" and "functional" and the like refer to a biological, chemical, mechanical, or therapeutic function.

"Hypochlorous acid", as used herein, refers to a weak acid having the chemical formula HClO. Hypochlorous acid is also known as chloric (I) acid, chloranol, or hydroxidochlorine. Salts of hypochlorite are also referred to herein and can include sodium hypochlorite (NaClO), calcium hypochlorite ($Ca(ClO)_2$), or potassium hypochlorite (KClO). As described herein, hypochlorous acid and hypochlorite are used as killing agents, skin cleansing agents, disinfectants, antibacterial agents, sanitizers, and/or preservatives. Hypochlorite, or acids and salts thereof, may be used in the lubricants and personal lubricants of the present invention at an amount of about 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is about 25% w/v. In some embodiments, the hypochlorite salt or hypochlorous acid is added directly to a personal lubricant, wherein the final amount of hypochlorite is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorite in the lubricant is between about 50 to about 100 ppm. In some embodiments, the amount of hypochlorite in the lubricant is about 75 ppm.

In some embodiments, the hypochlorite is added to the lubricant as a hypochlorite solution. In some embodiments, the hypochlorite solution is prepared from hypochlorite salt or hypochlorous acid. In some embodiments, the solution of hypochlorite is prepared by passing a sodium chloride solution through electrolysis. In some embodiments, the sodium chloride solution is a 0.1%, 0.15%, 0.2%, 0.25%, 0.3%, 0.35%, 0.4% or greater w/v % or within a range defined by any two of the aforementioned amounts. In some embodiments, the sodium chloride is 0.28%, and the resulting hypochlorite solution is 300 ppm. In some embodiments, the hypochlorite solution is added to the personal lubricant in an amount of about 0.5%, 1%, 5%, 10%, 15%, 20%, 25%, 30%, 40%, 50% or greater w/v %, or within a range defined by any two of the aforementioned amounts. In some embodiments, the solution includes, for example, about 300 ppm hypochlorite is added to a personal lubricant in an amount of about 25% w/v.

As used herein, silicone polymers include dimethicone, which is also known as polydimethylsiloxane (PDMS), dimethylpolysiloxane, E900, or polymerized siloxane and has the chemical formula of $CH_3[Si(CH_3)_2O]_nSi(CH_3)_3$ where n is the number of repeating monomer $[Si(CH_3)_2]$ units. Silicone polymers are used as an inert slip agent or lubricant. The silicone polymer may be used in the lubricant or personal lubricant in an amount of about 0.5%, 1%, 5%, 10%, 15%, 20%, 30%, 40%, 50%, or greater w/v %, or in an amount within any two of the aforementioned values or between a range defined by these values. In some embodiments, the amount of silicone polymer is about 10% w/v.

As used herein, the term "sodium magnesium silicate" refers to a silicate of sodium and magnesium and is a synthetic silicate clay, having magnesium and sodium silicate. It is used as a binder and bulking agent in cosmetics and personal care products, in part because of its ability to absorb water. It is also used in the creation of concrete. Sodium magnesium silicate is effective in slowing the decomposition of formulas, and can prevent premature darkening of the cosmetic composition and prevent premature development of a foul odor, thereby improving the shelf life of cosmetic compositions. In some embodiments, the sodium magnesium silicate is Laponite. As used herein, sodium magnesium silicate is useful as a gelling agent or rheology modifier. Sodium magnesium silicate may be used in the lubricant or personal lubricant in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of sodium magnesium silicate is about 3.25% w/v.

As used herein, the term "sodium phosphate monobasic" refers to the chemical formula of $NaH_2PO_4$, an inorganic compound of sodium with dihydrogen phosphate. Sodium phosphate monobasic is also referred to as sodium dihydrogen phosphate, sodium phosphate, monosodium phosphate, sodium biphosphate, acid sodium phosphate, monosodium orthophosphate, or primary sodium phosphate. As described herein, it may be used for adjustment of pH, as a thickening agent, or as an emulsifier. Sodium phosphate monobasic may be used in the lubricant or personal lubricant in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of sodium phosphate is about 3.25% w/v.

The personal lubricants described herein may further include an additive known in the art can be included. Exemplary additives include emollients, moisturizers, humectants, pigments, dyes, pearlescent compounds, nacreous pigments, bismuth oxychloride coated mica, titanium dioxide coated mica, colorants, fragrances, biocides, preservatives, alpha hydroxy acids, antioxidants, anti-microbial agents, anti-fungal agents, antiperspirant agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organo-modified clays and combinations thereof.

In some embodiments, the personal lubricant described herein is characterized in having an osmolality by vapor pressure of about 10, 20, 30, 35, 36, 37, 38, 39, 40, 41, 42, 43, 44, 45, 46, 47, 48, 49, 50, 55, 60, 70, 80, 90, or 100 mmol/kg, or within a range defined by any two of the aforementioned amounts. In some embodiments, the osmolality by vapor pressure is about 38 mmol/kg. In some embodiments, the osmolality by vapor pressure is about 49 mmol/kg. In some embodiments, the lubricant is characterized in having an osmolality by freezing point depression of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, or within a range defined by any two of the aforementioned amounts. In some embodiments, the osmolality by freezing point depression is about 22 mOsm/kg. In some embodiments, the osmolality by freezing point depression is about 54 mOsm/kg.

In some embodiments is provided a method of making the lubricant formulation. In some embodiments, the method includes providing hypochlorite. In some embodiments, the hypochlorite is provided as a hypochlorite acid or salt. In some embodiments, the hypochlorite is provided as a hypochlorite solution. In some embodiments, the method of making the lubricant includes providing hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is provided in an amount of about 50 to 100 ppm. In some embodiments, the hypochlorite is provided in an amount of about 75 ppm.

In some embodiments, the method of making the lubricant includes providing a hypochlorite solution. In some embodiments, the hypochlorite solution is prepared from hypochlorite acids or salts. In some embodiments, the hypochlorite salt is sodium hypochlorite. In some embodiments, the hypochlorite solution is prepared from sodium chloride. In some embodiments, the method includes running sodium chloride solution through electrolysis. In some embodiments, the sodium chloride solution is provided in an amount of about 0.1%, 0.15%, 0.2%, 0.25%, 0.3%, 0.35%, or 0.4% w/v. In some embodiments, the sodium chloride is 0.28%, and the resulting hypochlorite solution is about 300 ppm. In some embodiments, the method of making the lubricant includes diluting the hypochlorite solution to provide hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is provided in an amount of about 50 to 100 ppm. In some embodiments, the hypochlorite is provided in an amount of about 75 ppm.

In some embodiments, the method of making the lubricant further includes providing a silicone polymer. In some embodiments, the silicone polymer is dimethicone. In some embodiments, the silicone polymer is provided in an amount of about 0.5%, 1%, 5%, 10%, 15%, 20%, 30%, 40%, or 50% w/v, or within a range defined by any two of the aforementioned amounts. In some embodiments, the silicone polymer is provided in an amount of about 10% w/v.

In some embodiments, the method further includes providing an emulsifier. In some embodiments, the emulsifier is sodium phosphate. In some embodiments, the emulsifier is provided in an amount of about 0.05%, 0.1%, 0.2%, 0.3%, 0.4%, 0.5%, 1%, 1.5%, 2%, or 2.5% w/v or within a range defined by any two of the aforementioned amounts. In some embodiments, the emulsifier is provided in an amount of about 0.2% w/v.

In some embodiments, the method of making the lubricant further includes providing sodium magnesium silicate, water, or buffer or combinations thereof. In some embodiments, the sodium magnesium silicate is provided in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v or within a range defined by any two of the aforementioned amounts. In some embodiments, the sodium magnesium silicate is provided in an amount of about 3.25% w/v. In some embodiments, the water and/or buffer is provided in an amount to make up the balance of the lubricant, and is provided in an amount of about 20%, 30%, 40%, 45%, 50%, 55%, 56%, 57%, 58%, 59%, 60%, 61%, 61.55%, 62%, 62.5%, 63%, 65%, 70%, 75%, 80%, or 90% w/v or within a range defined by any two of the aforementioned amounts.

As used herein, the term "buffer" refers to a buffering agent and is used for balancing the pH and/or osmolality of the lubricant. Examples of a buffer for use herein include, for example, salts of phosphates, borates, citrates, ascorbates, carbonates, bicarbonates, TRIS, HEPES, sodium ions, potassium ions, chloride ions, bicarbonate ions, glucose, sucrose, peptides, proteins, a combination or mixture thereof or other agents that are chemically, functionally, or physiologically equivalent or similar. The lubricant compositions provided herein have an optimum pH and viscosity, with an osmolality that is hypo-osmotic, having an osmolality by vapor pressure of about 10, 20, 30, 35, 36, 37, 38, 39, 40, 41, 42, 43, 44, 45, 46, 47, 48, 49, 50, 55, 60, 70, 80, 90, or 100 mmol/kg, or within a range defined by any two of the aforementioned amounts. In some embodiments, the osmolality by vapor pressure is about 38 mmol/kg. In some embodiments, the osmolality by vapor pressure is about 49 mmol/kg. In some embodiments, the lubricant is characterized in having an osmolality by freezing point depression of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, or within a range defined by any two of the aforementioned amounts. In some embodiments, the osmolality by freezing point depression is about 22 mOsm/kg. In some embodiments, the osmolality by freezing point depression is about 54 mOsm/kg. The osmolality of the lubricant can be determined by vapor pressure osmometry or freezing point osmometry.

In some embodiments is provided a method of using a lubricant. In some embodiments, the method includes providing the lubricant and applying the lubricant. In some embodiments, the lubricant is provided as a ready-to-use formulation that includes hypochlorite or acids or salts thereof, silicone polymer, and an emulsifier, and further may include sodium magnesium silicate, water, or buffer. In some embodiments, the lubricant is provided in portions, and further additions and/or mixing is required prior to use. In some embodiments, the lubricant is applied in the penile or vaginal regions. In some embodiments, the lubricant is applied on a condom or other device. In some embodiments, the lubricant is applied multiple times daily, once daily, multiple times weekly, once weekly, multiple times monthly, or once monthly, or within a time frame defined by any two of the aforementioned time frames. In some embodiments, the lubricant is applied liberally. In some embodiments, the lubricant is applied meagerly.

In some embodiments, the personal lubricant as disclosed herein is useful for improving lubrication and comfort during sexual intimacy. In some embodiments, the personal lubricant described herein is a hybrid lubricant that includes both water and silicone. In some embodiments, the personal lubricant includes hypochlorite, or a salt or acid thereof, dimethicone, and an emulsifier. In some embodiments, the personal lubricant includes water and/or buffer, hypochlorous acid solution, dimethicone, sodium magnesium silicate, and sodium phosphate.

In some embodiments is provided a method of using a lubricant for the cessation, amelioration, prevention, or inhibition of the development of itching from the vagina or other body parts by eliminating microbial causing infections.

In some embodiments, the personal lubricant is useful for alleviating discomfort in a subject having inflammation or discomfort in the vaginal or vulvovaginal area. Symptoms can include but are not limited to irritation and/or itching of the genital area, inflammation of the vaginal or perineal area or pain. Causes can include but are not limited to disruption of the healthy microbiota, infections, yeast, bacteria or viruses. Pathogens that can cause irritation can include but are not limited to *Candida, Gardnerella*, gonorrhea, *chlamydia, Mycoplasma*, herpes, *Campylobacter*, or *Trichomonas vaginalis*. Irritation can also occur due to effects of diabetes, birth control, bad diet, tight clothing, use of antibiotics, hormonal vaginitis due to post-menopause or postpartum, or loss of estrogen. Irritants also originate from condoms, spermicides, soaps, perfumes, and lubricants. Loss of estrogen or hormonal vaginitis can also lead to dryness of tissues.

In some embodiments is provided a method of using the lubricant composition to stop a fungal infection. In some embodiments, the fungal infection is caused by a yeast of the *Candida* genus. In one embodiment, the yeast is of the *Candida albicans* species. In other embodiments, the *Candida* yeast may be of the *Candida dubliniensis, Candida parapsilosis, Candida tropicalis, Candida kerfyr, Candida guilliermondii, Candida inconspicua, Candida famata, Candida glabrata, Candida krusei, Candida lusitaniae*, or other *Candida* species, or combinations thereof. In some embodiments, the lubricant composition is used to stop a viral infection.

In some embodiments, the lubricant as disclosed herein is useful as a medical or surgical lubricant for use with medical instruments for insertion, penetration, or introduction of a catheter, ultra sound, or other medical device into a subject.

The invention is generally disclosed herein using affirmative language to describe the numerous embodiments. The invention also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1

Preparation of Personal Lubricant Formulations

The following example demonstrates the method of preparing the personal lubricant and various compositions or formulations thereof.

A personal lubricant was prepared with the ingredients as provided in Table 1. Hypochlorite or a salt or acid thereof was added to water, dimethicone, sodium magnesium silicate, and sodium phosphate in the preparation of a personal lubricant formulation PL-10.

TABLE 1

Personal Lubricant 10 (PL-10) Formulation

| Ingredient | Quantity |
| --- | --- |
| Water and/or buffer | balance |
| Hypochlorite | 75 ppm |
| Dimethicone | 10% w/v |
| Sodium Magnesium Silicate | 3.25% w/v |
| Sodium Phosphate | 0.2% w/v |

The personal lubricant formulation described in Table 1 was tested on various organisms associated with sexually transmitted diseases to determine the efficacy of inhibiting, eradication, or reducing the organismal population. Various microbial pathogens were tested, including human immunodeficiency virus (HIV), Herpes simplex virus (HSV), Hepatitis B virus (HBV), *Chlamydia trachomatis*, and *Neisseria gonorrhoeae*. These studies are described in detail in the following examples.

Alternative Preparation Example 1

A personal lubricant having 25% of a 220 ppm hypochlorite solution was added to 10% w/v dimethicone, with 3.25% w/v sodium magnesium silicate and 0.2% sodium phosphate, with the balance of 61.55% water. The hypochlorite solution was prepared by passing 0.28% sodium chloride through electrolysis to provide a 220 ppm hypochlorite solution.

Example 2

Efficacy of Personal Lubricant Against HIV-1 in Suspension

The following example shows the results of the efficacy of the personal lubricant against HIV-1 in suspension.

HIV-1 was evaluated in a virucidal suspension assay. The test medium was Roswell Park Memorial Institute-1640 (RPMI-1640) medium supplemented with 15% (v/v) heat-inactivated fetal bovine serum (FBS). The medium was also supplemented with 2.0 mM L-glutamine and 50 µg/mL gentamicin. The suspension containing HIV-1 was exposed to the personal lubricant formulation. At a pre-determined exposure time, an aliquot was removed, neutralized by serial dilution, and assayed for the presence of virus. The virus controls, cytotoxicity control, and neutralization control were assays in parallel. Antiviral properties of the personal lubricant were evaluated and compared at the specified concentrations and time intervals.

HIV-1 strain HTLV III$_B$ was exposed to a personal lubricant formulation, PL-10, for an exposure time of either 5 minutes or 10 minutes at a temperature of 20.0° C. in the presence of a 5% FBS organic soil load. PL-10 demonstrated a greater than 99.99% reduction in viral titer following 5 and 10 minute exposure times to HIV-1, as compared to the titer of the corresponding virus control. The 50% tissue culture infective dose (TCID$_{50}$)/200 µL, a measure of infectious virus titer, was less than $10^{2.50}$ at both 5 and 10 minutes. Table 2 summarizes the effects of exposure of the personal lubricant to a suspension of HIV-1. The cytotoxicity and neutralization control results are presented in Table 3. MT-2 (human T cell leukemia cells) were used as indicator cell cultures.

TABLE 2

Effects of PL-10 Against HIV-1 in Suspension

| | Virus Control | | HIV-1 + PL-10 | |
| --- | --- | --- | --- | --- |
| Dilution | 5 minute exposure | 10 minute exposure | 5 minute exposure | 10 minute exposure |
| Cell Control | 0 0 0 0 | 0 0 0 0 | 0 0 0 0 | 0 0 0 0 |
| $10^{-2}$ | + + + + | + + + + | T T T T | T T T T |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + + + + | 0 0 0 0 | 0 0 0 0 |
| $10^{-7}$ | 0 0 0 0 | 0 0 0 0 | 0 0 0 0 | 0 0 0 0 |
| TCID$_{50}$/200 µL | $10^{6.50}$ | $10^{6.50}$ | ≤$10^{2.50}$ | ≤$10^{2.50}$ |
| Percent Reduction | | | ≥99.99% | ≥99.99% |
| Log Reduction | | | ≥4.00 log$_{10}$ | ≥4.00 log$_{10}$ |

(+) = positive test for the presence of test virus
(0) = no test virus recovered and/or no cytotoxicity present
(T) = cytotoxicity present

TABLE 3

PL-10 Cytotoxicity and Neutralization Results for HIV-1

| | Cytotoxicity Control PL-10 | Neutralization Control HIV-1 + PL-10 |
| --- | --- | --- |
| Dilution | | |
| Cell Control | 0 0 0 0 | 0 0 0 0 |
| $10^{-2}$ | T T T T | T T T T |
| $10^{-3}$ | 0 0 0 0 | + + + + |
| $10^{-4}$ | 0 0 0 0 | + + + + |
| $10^{-5}$ | 0 0 0 0 | + + + + |
| $10^{-6}$ | 0 0 0 0 | + + + + |
| $10^{-7}$ | 0 0 0 0 | + + + + |
| TCID$_{50}$/200 µL | $10^{2.50}$ | *Neutralized at ≤2.50 Log$_{10}$ |

(+) = positive test for the presence of test virus
(0) = no test virus recovered and/or no cytotoxicity present
(T) = cytotoxicity present
(*) = Neutralization control reported as TCID$_{50}$/250 µL

Example 3

Efficacy of Personal Lubricant Against HSV-2 in Suspension

The following example shows the results of the efficacy of the personal lubricant against HSV-2 in suspension.

HSV-2 was evaluated in a virucidal suspension assay. The test medium was minimum essential medium (MEM)

supplemented with 5% (v/v) heat-inactivated FBS. The medium was also supplemented with 100 units/mL penicillin, 10 μg/mL gentamicin, and 2.5 μg/mL amphotericin B. HSV-2 was exposed to the personal lubricant formulation. At a pre-determined exposure time, an aliquot was removed, neutralized by serial dilution, and assayed for the presence of virus. The virus controls, cytotoxicity control, and neutralization control were assays in parallel. Antiviral properties of the personal lubricant were evaluated and compared at the specified concentrations and time intervals.

HSV-2, ATCC VR-734, Strain G was exposed to a personal lubricant formulation, PL-10. The exposure time was of either 5 minutes or 10 minutes at a temperature of 21.0° C. in the presence of a 5% FBS organic soil load. PL-10 demonstrated a greater than 99.9997% reduction in viral titer following 5 minute exposure time and a greater than 99.998% reduction in viral titer following a 10 minute exposure time to HSV-2, as compared to the titer of the corresponding virus control. The log reductions in viral titer were greater than 5.50 $\log_{10}$ and greater than 4.75 $\log_{10}$, respectively. Table 4 summarizes the effects of exposure of the personal lubricant to a suspension of HSV-2. The cytotoxicity and neutralization control results are presented in Table 5. Vero cells were used as indicator cell cultures.

TABLE 4

Effects of PL-10 Against HSV-2 in Suspension

| Dilution | Virus Control | | HSV-2 + PL-10 | |
| --- | --- | --- | --- | --- |
| | 5 minute exposure | 10 minute exposure | 5 minute exposure | 10 minute exposure |
| Cell Control | 0 0 0 0 | 0 0 0 0 | 0 0 0 0 | 0 0 0 0 |
| $10^{-2}$ | + + + + | + + + + | 0 0 0 0 | 0 0 0 0 |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + 0 + + | 0 0 0 0 | 0 0 0 0 |
| $10^{-7}$ | + 0 + 0 | 0 0 0 0 | 0 0 0 0 | 0 0 0 0 |
| 108 | 0 0 0 0 | 0 0 0 0 | 0 0 0 0 | 0 0 0 0 |
| $TCID_{50}/100\ \mu L$ | $10^{7.00}$ | $10^{6.25}$ | $\leq 10^{1.50}$ | $\leq 10^{1.50}$ |
| Percent Reduction | | | ≥99.9997% | ≥99.998% |
| Log Reduction | | | 5.50 $\log_{10}$ | 4.75 $\log_{10}$ |

(+) = positive test for the presence of test virus
(0) = no test virus recovered and/or no cytotoxicity present

TABLE 5

PL-10 Cytotoxicity and Neutralization Results for HSV-2

| Dilution | Cytotoxicity Control PL-10 | Neutralization Control HBV + PL-10 |
| --- | --- | --- |
| Cell Control | 0 0 0 0 | 0 0 0 0 |
| $10^{-2}$ | 0 0 0 0 | + + + + |
| $10^{-3}$ | 0 0 0 0 | + + + + |
| $10^{-4}$ | 0 0 0 0 | + + + + |
| $TCID_{50}/100\ \mu L$ | $\leq 10^{1.50}$ | *Neutralized at $\leq 1.50\ Log_{10}$ |

(+) = positive test for the presence of test virus
(0) = no test virus recovered and/or no cytotoxicity present
(*) = Neutralization control reported as $TCID_{50}/100\ \mu L$ Example 4

Efficacy of Personal Lubricant Against HBV in Suspension

The following example shows the results of the efficacy of the personal lubricant against HBV in suspension.

HBV was evaluated in a virucidal suspension assay. The test medium was Leibovitz L-15 medium supplemented with 0.1% glucose, 10 μM dexamethasone, 10 μg/mL insulin, 20 mM HEPES, 100 units/mL penicillin, and 10 μg/mL gentamicin. HBV was exposed to the personal lubricant formulation. At a pre-determined exposure time, an aliquot was removed, neutralized by serial dilution, and assayed for the presence of virus. The virus controls, cytotoxicity control, and neutralization control were assays in parallel. Antiviral properties of the personal lubricant were evaluated and compared at the specified concentrations and time intervals.

Duck HBV was exposed to a personal lubricant formulation, PL-10. The exposure time was of either 5 minutes or 10 minutes at a temperature of 20.0° C. in the presence of 100% duck serum, with no additional soil load added. PL-10 demonstrated a greater than 99.999% reduction in viral titer following 5 minute exposure time and a greater than 99.998% reduction in viral titer following a 10 minute exposure time to duck HBV, as compared to the titer of the corresponding virus control. The log reductions in viral titer were greater than 5.00 $\log_{10}$ and greater than 4.75 $\log_{10}$, respectively. Table 6 summarizes the effects of exposure of the personal lubricant to a suspension of HSV-2. The cytotoxicity and neutralization control results are presented in Table 7. Primary duck hepatocytes were used as indicator cell cultures.

TABLE 6

Effects of PL-10 Against HBV in Suspension

| Dilution | Virus Control | | HBV + PL-10 | |
| --- | --- | --- | --- | --- |
| | 5 minute exposure | 10 minute exposure | 5 minute exposure | 10 minute exposure |
| Cell Control | 0 0 0 0 | 0 0 0 0 | 0 0 0 0 | 0 0 0 0 |
| $10^{-2}$ | + + + + | + + + + | 0 0 0 0 | 0 0 0 0 |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + + + 0 | 0 0 0 0 | 0 0 0 0 |
| $10^{-7}$ | 0 0 0 0 | 0 0 0 0 | 0 0 0 0 | 0 0 0 0 |
| $TCID_{50}/250\ \mu L$ | $10^{6.50}$ | $10^{6.25}$ | $\leq 10^{1.50}$ | $\leq 10^{1.50}$ |
| Percent Reduction | | | ≥99.999% | ≥99.998% |
| Log Reduction | | | ≥5.00 $\log_{10}$ | ≥4.75 $\log_{10}$ |

(+) = positive test for the presence of test virus
(0) = no test virus recovered and/or no cytotoxicity present

TABLE 7

PL-10 Cytotoxicity and Neutralization Results for HBV

| Dilution | Cytotoxicity Control PL-10 | Neutralization Control HBV + PL-10 |
| --- | --- | --- |
| Cell Control | 0 0 0 0 | 0 0 0 0 |
| $10^{-2}$ | 0 0 0 0 | + + + + |
| $10^{-3}$ | 0 0 0 0 | + + + + |
| $10^{-4}$ | 0 0 0 0 | + + + + |
| $TCID_{50}/250\ \mu L$ | $\leq 10^{1.50}$ | *Neutralized at $\leq 1.50\ Log_{10}$ |

(+) = positive test for the presence of test virus
(0) = no test virus recovered and/or no cytotoxicity present
(*) = Neutralization control reported as $TCID_{50}/250\ \mu L$

Example 5

Efficacy of Personal Lubricant Against *Chlamydia* in Suspension

The following example shows the results of the efficacy of the personal lubricant against *Chlamydia trachomatis* in suspension.

*Chlamydia trachomatis* was evaluated in a chlamydial suspension assay. The test medium was MEM supplemented with 10% (v/v) heat-inactivated FBS, 2 µg/mL cycloheximide, 4.5 g/L glucose, 10 mM HEPES, 10 µg/mL gentamicin, and 2.5 µg/mL amphotericin B. A suspension of *chlamydia* was exposed to the personal lubricant formulation. At a pre-determined exposure time, an aliquot was removed, neutralized by serial dilution, and assayed for the presence of *chlamydia*. The *chlamydia* controls, cytotoxicity control, and neutralization control were assays in parallel. Antichlamydia properties of the personal lubricant were evaluated and compared at the specified concentrations and time intervals.

*Chlamydia trachomatis* (Serotype K), ATCC VR-887, strain UW-31/Cx was exposed to a personal lubricant formulation, PL-10. The exposure time was of either 5 minutes or 10 minutes at a temperature of 20.0° C. in the presence of 5% FBS organic soil load. PL-10 demonstrated a greater than 99.999% reduction in *chlamydia* titer following 5 minute exposure time and a greater than 99.998% reduction in *chlamydia* titer following a 10 minute exposure time to *Chlamydia trachomatis* (Serotype K), as compared to the titer of the corresponding *chlamydia* control. The log reductions in *chlamydia* titer were greater than 5.00 $\log_{10}$ and greater than 4.75 $\log_{10}$, respectively. Table 8 summarizes the effects of exposure of the personal lubricant to a suspension of *chlamydia*. The cytotoxicity and neutralization control results are presented in Table 9. McCoy indicator cell cultures were used.

TABLE 8

Effects of PL-10 Against *Chlamydia* in Suspension

| Dilution | *Chlamydia* Control 5 minute exposure | *Chlamydia* Control 10 minute exposure | *Chlamydia trachomatis* + PL-10 5 minute exposure | *Chlamydia trachomatis* + PL-10 10 minute exposure |
|---|---|---|---|---|
| Cell Control | 0 0 0 0 | 0 0 0 0 | 0 0 0 0 | 0 0 0 0 |
| $10^{-2}$ | + + + + | + + + + | 0 0 0 0 | 0 0 0 0 |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + + 0 + | 0 0 0 0 | 0 0 0 0 |
| $10^{-7}$ | 0 0 0 0 | 0 0 0 0 | 0 0 0 0 | 0 0 0 0 |
| $TCID_{50}$/200 µL | $10^{6.50}$ | $10^{6.25}$ | $\leq 10^{1.50}$ | $\leq 10^{1.50}$ |
| Percent Reduction | | | ≥99.999% | ≥99.998% |
| Log Reduction | | | ≥5.00 $\log_{10}$ | ≥4.75 $\log_{10}$ |

(+) = positive test for the presence of test *chlamydia*
(0) = no test *chlamydia* recovered and/or no cytotoxicity present

TABLE 9

PL-10 Cytotoxicity and Neutralization Results for *Chlamydia*

| Dilution | Cytotoxicity Control PL-10 | Neutralization Control *Chlamydia trachomatis* + PL-10 |
|---|---|---|
| Cell Control | 0 0 0 0 | 0 0 0 0 |
| $10^{-2}$ | 0 0 0 0 | + + + + |
| $10^{-3}$ | 0 0 0 0 | + + + + |
| $10^{-4}$ | 0 0 0 0 | + + + + |
| $TCID_{50}$/100 µL | $<10^{1.50}$ | *Neutralized at ≤1.50 $\log_{10}$ |

(+) = positive test for the presence of test *chlamydia*
(0) = no test *chlamydia* recovered and/or no cytotoxicity present
(*) = Neutralization control reported as $TCID_{50}$/200 µL

Example 6

Efficacy of Personal Lubricant Against *Neisseria Gonorrhoeae* in Suspension The following example shows the results of the efficacy of the personal lubricant against *Neisseria gonorrhoeae* in suspension.

*Neisseria gonorrhoeae* was evaluated in a time kill assay. The test was conducted in an agar plate medium of chocolate agar. *Neisseria gonorrhoeae*, ATCC 43069, was exposed to a personal lubricant formulation, PL-10 at exposure times of 1, 2, 5, and 10 minutes in suspension at a temperature of 21.0° C. After exposure, an aliquot of the suspension was transferred to a neutralizer and was assayed for survivors. Appropriate culture purity, neutralizer sterility, test population, and neutralization confirmation controls were performed. The neutralizer was Letheen broth with 0.07% lecithin and 0.5% Tween 80.

The neutralizer sterility control shows no growth of *Neisseria gonorrhoeae*. The control population of *Neisseria gonorrhoeae* shows $3.2 \times 10^4$ colony forming units, and log reduction of 4.51 $\log_{10}$. The exposure of *Neisserria gonorrhoeae* to PL-10 for any of 1, 2, 5, and 10 minutes showed no survivors at any of the dilution. Table 10 summarizes the effects of exposure for PL-10 against *Neisseria gonorrhoeae*.

TABLE 10

PL-10 Against *Neisseria gonorrhoeae*

| Exposure Time (minutes) | CFU/mL in Test population control ($\log_{10}$) | CFU/ mL of Survivors | $\log_{10}$ Survivors | Percent Reduction | $\log_{10}$ Reduction |
|---|---|---|---|---|---|
| 1 | 3.2 × $10^4$ (4.51) | <5 | <0.70 | >99.9% | >3.81 |
| 2 | | <5 | <0.70 | >99.9% | >3.81 |
| 5 | | <5 | <0.70 | >99.9% | >3.81 |
| 10 | | <5 | <0.70 | >99.9% | >3.81 |

CFU = colony forming units

Table 11 summarizes the results of Examples 2-6 for the efficacy of PL-10 in reducing a variety of organismal populations.

TABLE 11

PL-10 Destroys Major Sexually Transmitted Infections

| Test Organism | Max Control Population | Population at 5 minute exposure | Percent Reduction | Population at 10 minute exposure | Percent Reduction |
|---|---|---|---|---|---|
| HIV-1 | 4.00 Log10 | 0 | >99.99% | 0 | >99.99% |
| Herpes simplex virus type 2 | 5.50 Log10 | 0 | >99.9997% | 0 | >99.998% |
| Hepatitis B virus | 5.00 Log10 | 0 | >99.999% | 0 | >99.998% |
| *Chlamydia trachomatis* | 5.00 Log10 | 0 | >99.999% | 0 | >99.998% |
| *Neisseria gonorrhoeae* | 3.8 Log10 | 0 | >99.9% | 0 | >99.9% |

Example 7

Cytotoxicity of Personal Lubricant on Cell Culture

The following example shows the results of the cytotoxicity of the personal lubricant on cell cultures.

The personal lubricant PL-10 was added to mouse fibroblast cells and incubated for 24 hours. The cells were observed under 100× magnification and the amount of morphology was scored using a 0-4 scale, where 0=no reactivity and 4=severe reactivity. A score of 3 or greater indicates a cytotoxic effect. The personal lubricant received a score of 2, indicating that the personal lubricant is not cytotoxic on mouse fibroblast cultures.

Example 8

Sensitivity Test of Personal Lubricant

The following example shows the results of the sensitivity of the personal lubricant on animal models.

The personal lubricant was tested on guinea pigs to determine if exposure to the product produced a delayed-type hypersensitivity skin reaction. In this example, guinea pigs were exposed to the personal lubricant and to a control substance both underneath the skin and topically. After 14 days, the animals were again exposed to the lubricant or control. The test sites on the skin were evaluated at both 24 and 48 hours post treatment. No sensitization reactions were observed, and the test group did not exhibit differences from the control group.

Example 9

Vaginal Mucosal Irritation Test of Personal Lubricant

The following example shows the results of the personal lubricant on vaginal mucosal irritation. The personal lubricant of Example 1, PL-10, was used on rabbits to determine the effects of the personal lubricant on vaginal tissue. The study complied with all applicable sections of the Final Rules of the Animal Welfare Act regulations (9 CFR 1-3), the Public Health Service Policy on Humane Care and Use of Laboratory Animals, and the Guide for the Care and Use of Laboratory Animals. Test procedures were reviewed and approved by PBL's Institutional Animal Care and Use Committee (IACUC) in compliance with Animal Welfare Act.

Environment. New Zealand white rabbits were housed individually in stainless steel cages. Animals were maintained in a controlled environment at a nominal temperature range of 16 to 22° C., a humidity range of 50 □ 20%, and a light/dark cycle of 12 hours. Animals were maintained in rooms with at least ten room air changes per hour.

Diet and Feed. Animals received a Certified Laboratory Rabbit Diet approximately 165 g per day. The feed is analyzed by the supplier for nutritional components and environmental contaminants. There are no known contaminants in the feed that interfered with the conduct of this example.

Water. Fresh, potable drinking water was provided ad libitum to all animals via a sipper tube. Water testing is conducted two times a year for total dissolved solids and specified microbiological content and selected elements, heavy metals, organophosphates, and chlorinated hydrocarbons. There are no known contaminants in the water that interfered with the conduct of this example.

Acclimation. Animals placed on study were acclimated to the testing facility for at least 6 days prior to initiation of the study. Health observations were performed prior to the study to ensure that the animals were acceptable for study use.

Assignment to Study and Disposition. Animals were examined prior to study initiation, and determined (based on clinical observations) suitable as test subjects.

Test and Control Article Preparation: The personal lubricant PL-10 is applied. Physiological saline (SCI) is used as a negative control.

Procedure: Six female rabbits were used in this example (three test and three control animals). Prior to the test and prior to each treatment, the animals were checked for vaginal discharge, swelling and/or other evidence of vaginal infection, irritation or injury. The animals were weighed prior to the initial dosing and at the termination of the test. Rabbits were dosed at 24±2 hour intervals every day for a minimum of five consecutive days (Days 0, 1, 2, 3 and 4). A short, soft catheter (approximately 6 cm) or blunt-tipped cannula (for example, 12 French Nelaton catheter) attached to a syringe was used for administration of the personal lubricant. The dose volume was approximately 1 mL. The tip of the catheter used for the test group animals was moistened with the personal lubricant and inserted into vagina. The tip of the catheter used for the control group animals was moistened with a control lubricant (for example, Lubrivet) and inserted into the vagina. The personal lubricant or control (at least 1 mL) was introduced no more than 6 cm into the anterior vagina. Any expelled material was gently removed with a soft tissue and rabbit returned to its cage.

Clinical Observation: At 24±2 hours after the initial application and immediately prior to each treatment, the appearance of the vaginal opening and perineum was noted for signs of discharge, erythema and edema. At 24±2 hours after the last dose, all animals were euthanized. The entire urogenital tract (including the vagina and the cervix) was removed. The entire vagina was opened longitudinally, and examined for gross evidence of irritation, injury to epithelial layer of tissue and necrosis. The entire urogenital tract was placed in 10% formalin and samples further processed by approved histopathology laboratory (for example, HSRL, VA). Histopathological evaluation of tissues was performed by a Board Certified Pathologist. The vaginal tissues were evaluated for the irritant effects.

Results: No evidence of mucosal irritation was found in the test animals following vaginal exposure to the personal lubricant, based on both macroscopic (evidence of irritation, epithelial cell injury, and necrosis) and microscopic (histopathological) analysis.

Example 10

Acute Systemic Toxicity of Personal Lubricant

The following example shows that the personal lubricant described herein does not show systemic toxicity in mice.

Mice were injected intraperitoneally with the personal lubricant and observed for 3 days. None of the animals tested exhibited any biological reactivity during the test period, including no difference in body weight, no signs of dehydration, no abnormal posture or appearance of skin, eyes, fur and mucous membranes, no change in urine and fecal output, and no change in locomotor behavior.

Example 11

Condom Compatibility of Personal Lubricant

The following example demonstrates that the personal lubricant as described herein is compatible with a variety of condoms in terms of being compatible with standard condom testing measures, such as burst pressure, burst volume, break force, and elongation.

The personal lubricant was tested with latex, polyisoprene, and polyurethane condoms. As a baseline, each condom was tested as received, with no heat or lubricant applied. A control was performed with each condom exposed to 40° C. for 1 hour, without lubricant. A positive control was performed with each condom exposed to 40° C. for 1 hour with mineral oil applied. The test was performed at 40° C. for 1 hour with the personal lubricant, PL-10. Test results indicate that the personal lubricant passed all natural latex and polyisoprene condom compatibility testing.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A personal lubricant, comprising:
   hypochlorite;
   an emulsifier comprising sodium magnesium silicate;
   a silicone polymer; and
   a buffer.

2. The personal lubricant of claim 1, wherein the hypochlorite is present in an amount of about 50 to about 100 ppm.

3. The personal lubricant of claim 2, wherein the hypochlorite is present in an amount of about 75 ppm.

4. The personal lubricant of claim 1, wherein the buffer is present in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, or 15% w/v.

5. The personal lubricant of claim 4, wherein the buffer is present in an amount of about 0.2% w/v.

6. The personal lubricant of claim 1, wherein the silicone polymer is dimethicone.

7. The personal lubricant of claim 1, wherein the sodium magnesium silicate is present in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v.

8. The personal lubricant of claim 7, wherein the sodium magnesium silicate is present in an amount of about 3.25% w/v.

9. The personal lubricant of claim 1, wherein the silicone polymer is present in an amount of about 0.5%, 1%, 5%, 10%, 15%, 20%, 30%, 40%, or 50% w/v.

10. The personal lubricant of claim 9, wherein the silicone polymer is present in an amount of about 10% w/v.

11. The personal lubricant of claim 1, wherein the buffer is sodium phosphate.

12. The personal lubricant of claim 1, further comprising water.

13. The personal lubricant of claim 1, wherein the lubricant has an osmolality of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, as measured by freezing point osmometry.

14. The personal lubricant of claim 13, wherein the lubricant has an osmolality of about 22 mOsm/kg, as measured by freezing point osmometry.

15. The personal lubricant of claim 13, wherein the lubricant has an osmolality of about 54 mOsm/kg, as measured by freezing point osmometry.

16. A method for increasing comfort and lubricity, comprising supplying the personal lubricant of claim 1.

17. The personal lubricant of claim 1, wherein the hypochlorite is in an amount of about 75 ppm, wherein the silicone polymer comprises dimethicone in an amount of about 10% w/v, wherein the emulsifier comprises sodium phosphate in an amount of about 0.2% w/v, and wherein the lubricant comprises sodium magnesium silicate in an amount of about 3.25% w/v, and water in an amount of about 61.55% w/v.

18. A method for increasing comfort and lubricity, comprising supplying the personal lubricant of claim 17.

19. A method of making the personal lubricant of claim 17, comprising providing a hypochlorite solution and a silicone polymer and mixing the ingredients to form a lubricant.

* * * * *